(12) United States Patent
Yang

(10) Patent No.: US 7,736,780 B2
(45) Date of Patent: Jun. 15, 2010

(54) FUEL CELL MEMBRANE CONTAINING ZIRCONIUM PHOSPHATE

(75) Inventor: Zhen-Yu Yang, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1159 days.

(21) Appl. No.: 10/566,940

(22) PCT Filed: May 21, 2004

(86) PCT No.: PCT/US2004/016431
§ 371 (c)(1),
(2), (4) Date: Feb. 13, 2006

(87) PCT Pub. No.: WO2004/106349
PCT Pub. Date: Dec. 9, 2004

(65) Prior Publication Data
US 2006/0275636 A1      Dec. 7, 2006

(51) Int. Cl.
*H01M 8/10* (2006.01)
(52) U.S. Cl. .......................... 429/33; 429/30
(58) Field of Classification Search ............ 429/40
See application file for complete search history.

(56) References Cited

U.S. PATENT DOCUMENTS

| 3,664,915 A | 5/1972 | Gore |
| 3,953,566 A | 4/1976 | Gore |
| 3,962,153 A | 6/1976 | Gore |
| 4,187,390 A | 2/1980 | Gore |

FOREIGN PATENT DOCUMENTS

| EP | 1 191 621 A2 | 3/2002 |
| WO | WO 92/18592 A1 | 10/1992 |

OTHER PUBLICATIONS

P. Costamagna et. al., Nafion 115/Zirconium Phosphate Composite Membranes for Operation of PEMFC'S Above 100 C, Electrochimica ACTA, 2002, vol. 47:1023-1033.

*Primary Examiner*—Dah-Wei D Yuan
*Assistant Examiner*—Adam A Arciero

(57) ABSTRACT

The present invention provides for a compound having the following structure: $Zr(O_3PZ_qY_nX)_{2-m}(O3PR)_m$, wherein X=a functional group such as $CO_2H$, $PO(OH)_2$, and $SO_3H$, and $SO_2NHSO_2W$, wherein W=aryl of 6 to 10 carbon atoms or Y; Y=perfluoro-linear, branched or cyclic alkylene group, wherein the alkylene is 1-20 carbon atoms, or a fluorinated group containing at least one substituent selected from the group consisting of oxygen, chlorine and bromine; Z=alkylene of 1-12 carbon atoms, aryl of 6-10 carbon atoms, or a heterocyclic aryl group of 3-10 carbons atoms; R=alkyl of 1-12 carbon atoms, aryl of 6-10 carbon atoms, substituted alkyl, or substituted aryl, wherein the substituent is selected from the group consisting of F, Cl, perfluoroalkyl, alkyl of 1-12 carbon atoms and aryl of 6-10 carbon atoms; n=0 or 1; q=0 or 1; and m=0 to 1.5; with the proviso that when n=0, and q=1, Z=at least one heterocyclic group having 3 to 10 carbon atoms, 1 to 5 nitrogen atoms and 0 to 4 oxygen atoms. The invention also provides a polymer electrolyte membrane, a catalyst coated membrane and a fuel cell having this compound.

34 Claims, 1 Drawing Sheet

FUEL CELL MEMBRANE CONTAINING ZIRCONIUM PHOSPHATE

FIELD OF THE INVENTION

The present invention relates to a novel compound and its use in electrochemical cells as an electrolyte, and more particularly to the use of the compound in fuel cells.

BACKGROUND OF THE INVENTION

Electrochemical cells, such as fuel cells and lithium-ion batteries are known. Depending on the operating conditions, each type of cell places a particular set of requirements upon the electrolytes used in them. For fuel cells, this is typically dictated by the type of fuel, such as hydrogen or methanol, used to power the cell and the composition of the membrane used to separate the electrodes. Proton-exchange membrane fuel cells, powered by hydrogen as the fuel, could be run at higher operating temperatures than currently employed to take advantage of lower purity feed streams, improved electrode kinetics, better heat transfer from the fuel cell stack to improve its cooling. Waste heat is also employed in a useful fashion. However, if current fuel cells are to be operated at greater than 100° C. then they must be pressurized to maintain adequate hydration of typical proton-exchange membranes, such as DuPont Nafion® perfluorosulfonic acid membrane, to support useful levels of proton conductivity.

There is an ongoing need to discover novel electrolytes that improve the performance of the latest generation of electrochemical cells, such as fuel cells and lithium-ion batteries, and form membrane materials that maintain adequate proton conductivity at lower levels of hydration.

SUMMARY OF THE INVENTION

In a first aspect, the invention provides a compound having the following structure:

$$Zr(O_3PZ_qY_nX)_{2-m}(O_3PR)_m$$

wherein

X=a functional group selected from the group consisting of $CO_2H$, $PO(OH)_2$, $SO_3H$, and $SO_2NHSO_2W$, wherein W=aryl of 6 to 10 carbon atoms or Y;

Y=perfluoro-linear, branched or cyclic alkylene group, wherein the alkylene is 1-20 carbon atoms, or a fluorinated group containing at least one substituent selected from the group consisting of oxygen, chlorine and bromine;

Z=alkylene of 1-12 carbon atoms, aryl of 6-10 carbon atoms, or a heterocyclic aryl group of 3-10 carbons atoms;

R=alkyl of 1-12 carbon atoms, aryl of 6-10 carbon atoms, substituted alkyl, or substituted aryl, wherein the substituent is selected from the group consisting of F, Cl, perfluoroalkyl, alkyl of 1-12 carbon atoms and aryl of 6-10 carbon atoms;

n=0 or 1;

q=0 or 1; and m=0 to 1.5; with the proviso that when n=0, and q=1, Z=at least one heterocyclic group having 3 to 10 carbon atoms, 1 to 5 nitrogen atoms and 0 to 4 oxygen atoms.

In a second aspect, the invention provides a functionalized phosphonic acid having the following structure:

$$(HO)_2OPZ_qY_nX.$$

wherein

X=a functional group selected from the group consisting of $CO_2H$, $PO(OH)_2$, $SO_3H$, and $SO_2NHSO_2W$, wherein W=aryl of 6 to 10 carbon atoms or Y;

Y=perfluoro-linear, branched or cyclic alkylene group, wherein the alkylene is 1-20 carbon atoms, or a fluorinated group containing at least one substituent selected from the group consisting of oxygen, chlorine and bromine;

Z=alkylene of 1-12 carbon atoms, aryl of 6-10 carbon atoms, or a heterocyclic aryl group of 3-10 carbons atoms;

n=0 or 1; and q=0 or 1; with the proviso that when n=0, and q=1, Z=at least one heterocyclic group having 3 to 10 carbon atoms, 1 to 5 nitrogen atoms and 0 to 4 oxygen atoms.

In a third aspect, the invention provides a solid electrolyte membrane comprising a compound having the following structure:

$$Zr(O_3PZ_qY_nX)_{2-m}(O_3PR)_m$$

wherein

X=a functional group selected from the group consisting of $CO_2H$, $PO(OH)_2$, $SO_3H$, and $SO_2NHSO_2W$, wherein W=aryl of 6 to 10 carbon atoms or Y;

Y=perfluoro-linear, branched or cyclic alkylene group, wherein the alkylene is 1-20 carbon atoms, or a fluorinated group containing at least one substituent selected from the group consisting of oxygen, chlorine and bromine;

Z=alkylene of 1-12 carbon atoms, aryl of 6-10 carbon atoms, or a heterocyclic aryl group of 3-10 carbons atoms;

R=alkyl of 1-12 carbon atoms, aryl of 6-10 carbon atoms, substituted alkyl, or substituted aryl, wherein the substituent is selected from the group consisting of F, Cl, perfluoroalkyl, alkyl of 1-12 carbon atoms and aryl of 6-10 carbon atoms;

n=0 or 1;

q=0 or 1; and m=0 to 1.5; with the proviso that when n=0, and q=1, Z=at least one heterocyclic group having 3 to 10 carbon atoms, 1 to 5 nitrogen atoms and 0 to 4 oxygen atoms. These membranes are particularly useful at temperatures of at least 100° C. Typically the compound is imbibed into a porous support to form the solid polymer electrolyte membrane.

In a fourth aspect, the invention provides a catalyst coated membrane comprising a solid electrolyte membrane having a first surface and a second surface, an anode present on the first surface of the solid electrolyte membrane, and a cathode present on the second surface of the solid electrolyte membrane, wherein the solid electrolyte membrane comprises a compound having the following structure:

$$Zr(O_3PZ_qY_nX)_{2-m}(O_3PR)_m$$

wherein

X=a functional group selected from the group consisting of $CO_2H$, $PO(OH)_2$, $SO_3H$, AND $SO_2NHSO_2W$, wherein W=aryl of 6 to 10 carbon atoms or Y;

Y=perfluoro-linear, branched or cyclic alkylene group, wherein the alkylene is 1-20 carbon atoms, or a fluorinated group containing at least one substituent selected from the group consisting of oxygen, chlorine and bromine;

Z=alkylene of 1-12 carbon atoms, aryl of 6-10 carbon atoms, or a heterocyclic aryl group of 3-10 carbons atoms;

R=alkyl of 1-12 carbon atoms, aryl of 6-10 carbon atoms, substituted alkyl, or substituted aryl, wherein the substituent is selected from the group consisting of F, Cl, perfluoroalkyl, alkyl of 1-12 carbon atoms and aryl of 6-10 carbon atoms;

n=0 or 1;

q=0 or 1; and m=0 to 1.5; with the proviso that when n=0, and q=1, Z=at least one heterocyclic group having 3 to 10 carbon atoms, 1 to 5 nitrogen atoms and 0 to 4 oxygen atoms. The compound may be introduced into the membrane by various methods, e.g. by imbibing into a porous support.

In a fifth aspect, the invention provides a fuel cell comprising a solid electrolyte membrane having a first surface and a second surface, wherein the solid electrolyte membrane comprises a compound having the following structure:

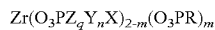

wherein

X=a functional group selected from the group consisting of $CO_2H$, $PO(OH)_2$, $SO_3H$, and $SO_2NHSO_2W$, wherein W=aryl of 6 to 10 carbon atoms or Y;

Y=perfluoro-linear, branched or cyclic alkylene group, wherein the alkylene is 1-20 carbon atoms, or a fluorinated group containing at least one substituent selected from the group consisting of oxygen, chlorine and bromine;

Z=alkylene of 1-12 carbon atoms, aryl of 6-10 carbon atoms, or a heterocyclic aryl group of 3-10 carbons atoms;

R=alkyl of 1-12 carbon atoms, aryl of 6-10 carbon atoms, substituted alkyl, or substituted aryl, wherein the substituent is selected from the group consisting of F, Cl, perfluoroalkyl, alkyl of 1-12 carbon atoms and aryl of 6-10 carbon atoms;

n=0 or 1;

q=0 or 1; and m=0 to 1.5; with the proviso that when n=0, and q=1, Z=at least one heterocyclic group having 3 to 10 carbon atoms, 1 to 5 nitrogen atoms and 0 to 4 oxygen atoms.

In the fifth aspect, the fuel cell further comprises an anode and a cathode present on the first and second surfaces of the electrolyte membrane. Gas diffusion backings may be present on the side of the anode or cathode away from the solid polymer electrolyte membrane. Alternately, gas diffusion electrodes comprising a gas diffusion backing and an electrode may be present on the first and second surfaces of the solid polymer electrolyte membrane, wherein the electrode is adjacent the solid polymer electrolyte membrane.

In the fifth aspect, the fuel cell further comprises a means for delivering fuel to the anode, a means for delivering oxygen to the cathode, a means for connecting the anode and cathode to an external electrical load, methanol in the liquid or gaseous state in contact with the anode, and oxygen in contact with the cathode. The fuel is in the liquid or vapor phase. Some suitable fuels include hydrogen, and alcohols such as methanol and ethanol, etc.

DETAILED DESCRIPTION OF THE INVENTION

Figure 1:
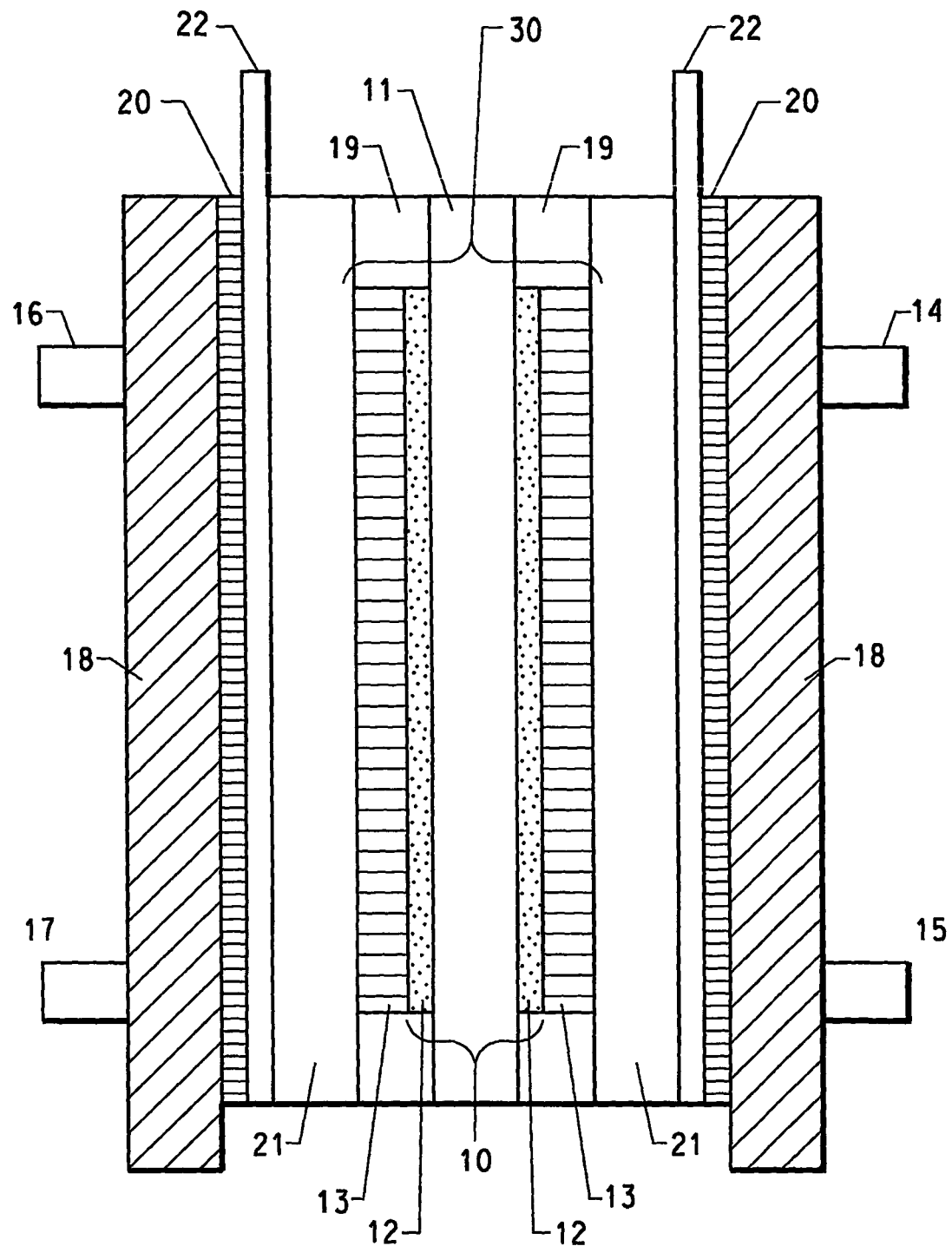
FIG. 1 is a schematic illustration of a single cell assembly.

The compounds of the invention that may be small molecules are useful as electrolytes in the preparation of the solid electrolyte membranes. These solid electrolyte membranes may be used to make catalyst coated membranes that are a component of fuel cells.

Compound:

The compound of the invention has the following structure:

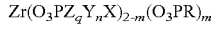

wherein

X=a functional group selected from the group consisting of $CO_2H$, $PO(OH)_2$, $SO_3H$, AND $SO_2NHSO_2W$; wherein W=aryl of 6 to 10 carbon atoms or —Y;

Y=perfluoro-linear, branched or cyclic alkylene group, wherein the alkylene is 1-20 carbon atoms such as perfluoromethylene, perfluoroethylene, perfluoropropylene or a fluorinated group containing at least one substituent selected from the group consisting of oxygen, chlorine and bromine selected from the group consisting of $CF_2CF_2OCF_2CF_2$ or $CF_2CFCF_3OCF_2CF_2$;

Z=alkylene of 1-12 carbon atoms such as methylene, ethylene and propylene, aryl of 6-10 carbon atoms such as phenyl, or substituted phenyl, wherein the substituent is selected from the group consisting of, F, Cl, perfluoroalkyl such as trifluoromethyl, pentafluoroethyl, alkyl of 1-12 carbon atoms such as methyl, ethyl, propyl, butyl; naphthalene; or a heterocyclic aryl group of 3-10 carbons atoms such as benzimidazole, imidazole, pyrazole, triazole, thiazole, or oxadiazole; R=alkyl of 1-12 carbon atoms such as methylene, ethylene and propylene; aryl of 6-12 carbon atoms such as benzene, or substituted benzene, naphthalene or substituted naphthalene; wherein the substituent is selected from the group consisting of F, Cl, perfluoroalkyl such as trifluoromethyl, pentafluoroethyl, alkyl of 1-12 carbon atoms such as methyl, ethyl, propyl, butyl, more typically methyl, and aryl of 6-12 carbon atoms such as benzene, or substituted benzene, wherein the substituent is selected from the group consisting of F, Cl, perfluoroalkyl such as trifluoromethyl, pentafluoroethyl, and alkyl of 1-12 carbon atoms such as methyl, ethyl, propyl, butyl;

n=0 or 1;

q=0 or 1;

m=0 to 1.5; and with the proviso that when n=0, and q=1, Z=heterocyclic groups having 3 to 12 carbon atoms such as benzimidazole, imidazole, pyrazole, triazole, thiazole, or oxadiazole; more typically 3 to 8 carbon atoms, 1 to 5 nitrogen atoms, more typically 2 to 3 nitrogen atoms, and 0 to 4 oxygen atoms, more typically 0 to 2 oxygen atoms.

Some suitable heterocyclic groups include, benzimidazole, imidazole or oxadiazole. Some suitable compounds include $Zr(HO_2CCF_2CH_2CH_2CH_2PO_3)_2$, $Zr(H_2O_3PCF_2CH_2CH_2CH_2PO_3)_2$, $Zr(HO_3SCF_2CF_2OCF_2CF_2CH_2CH_2CH_2PO_3)_2$, Zirconium (2-benzimidazolyl-2-ethylphosphonate), Zirconium(2-imidazolyl-2-ethylphosphonate), Zirconium(2-pyrazolyl-2-ethylphosphonate), Zirconium(2-oxadiazolyl-2-ethylphosphonate)

The compound may be prepared by several reaction steps from iodo substituted perfluoroalkylene functionalized compounds such as $IR_FX'$, where $R_F$ is perfluoro-linear, branched or cyclic alkylene group, wherein the alkylene is 1-20 carbon atoms such as perfluoromethylene, perfluoroethylene or a fluorinated group containing substituents selected from the group consisting of oxygen, chlorine and bromine such as 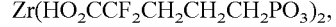 $CF_2CF_2OCF_2CF_2$, $CF_2CFCF_3OCF_2CF_2$, and X' is a precursor group such as $SO_2F$, $PO(OEt)_2$ or $CO_2Et$ of functionalized groups X, such as $SO_3H$, $SO_2NSO_2CF_3$, $PO(OH)_2$, $CO_2H$. Addition of $IR_FX'$ to alkenylphosphonates such as diethyl allylphosphonate gives the corresponding adducts with a radical initiator such as benzoyl peroxide or metals such as Cu and $Pd(PPh_3)_4$ or salts such as $Na_2S_2O_4$. Adducts were reduced to remove iodine with a reducing reagent such as Bu$_3$SnH, Zn/HCl, Zn/NiCl$_2$ and so on. Finally, hydrolysis of the phosphonate with aqueous acid such as aqueous HCl produced the corresponding phosphonic acid, which reacted with ZrOCl$_2$ in acidic water to give a compound Zr[O$_2$POR'CH$_2$CH$_2$R$_F$X]$_2$.

In the presence of other phosphonic acids, the mixed Zirconium phosphonate was formed as shown by this reaction:

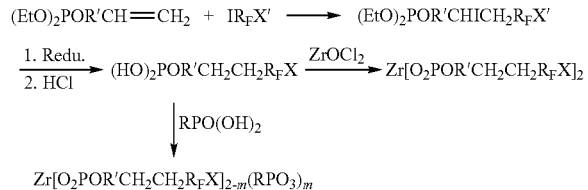

Alternatively, functionalized phosphonic acid may be directly reacted with ZrOCl$_2$ in acidic water. This is particularly used for the production of Zr phosphonate containing heterocyclic ring structures such as benzimidazole, imidazole, pyrazole, triazole, thiazole, or oxadiazole; A typical example includes the following:

supports made from hydrocarbons such as a polyolefin, e.g., polyethylene, polypropylene, polybutylene, copolymers of those materials, and the like. Perhalogenated polymers such as polychlorotrifluoroethylene may also be used. For resistance to thermal and chemical degradation, the support typically is made of a highly fluorinated polymer, most preferably perfluorinated polymer.

For example, the polymer for the porous support can be a microporous film of polytetrafluoroethylene (PTFE) or a copolymer of tetrafluoroethylene with other perfluoroalkyl olefins or with perfluorovinyl ethers. Microporous PTFE films and sheeting are known which are suitable for use as a support layer. For example, U.S. Pat. No. 3,664,915 discloses uniaxially stretched film having at least 40% voids. U.S. Pat. Nos. 3,953,566, 3,962,153 and 4,187,390 disclose porous PTFE films having at least 70% voids.

Alternatively, the porous support may be a fabric made from fibers of the support polymers discussed above woven using various weaves such as the plain weave, basket weave, leno weave, or others. A membrane suitable for the practice of the invention can be made by coating the porous support fabric with the compound, also known as the electrolyte, of the invention to form a composite membrane. To be effective

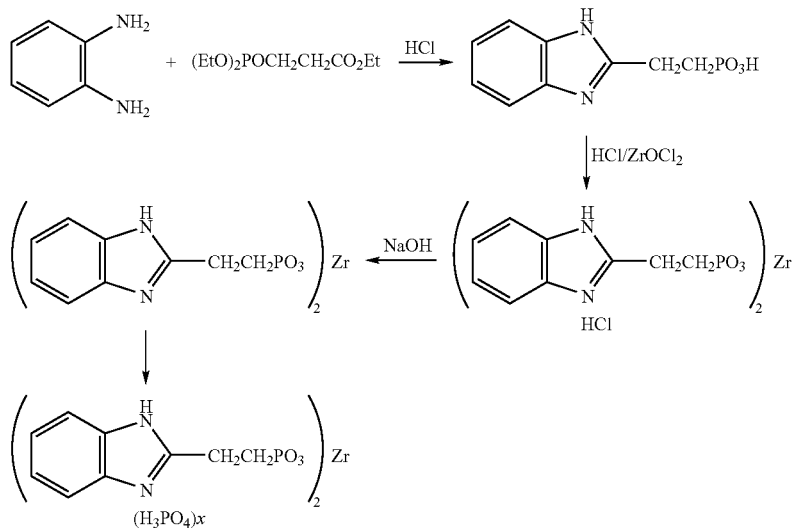

Membrane:

The compound identified above is useful in forming a solid electrolyte membrane, typically capable of operating at a temperature of at least 100° C. In a first method, the electrolyte may be directly pressed into thin films or a mixture of the electrolyte with other thermally and chemically stable polymers may be pressed into a film.

In a second method the electrolyte may be ground to a fine powder, and then dispersed in polymeric solution such as polyvinylidene fluoride in organic solvent. The dispersion may then be cast into a thin film on a glass plate and baked to remove solvent.

In a third method a mixture of the electrolyte and optionally a crosslinkable monomer may be poured into a porous support followed by drying, with or without heat, to insure that the electrolyte stayed in the porous structure.

The porous support of the membrane may be made from a wide range of components. Some examples include porous the coating should typically be on both the outside surfaces as well as distributed through the internal pores of the support. This may be accomplished by impregnating the porous support with a solution or dispersion of the solid electrolyte, using a solvent that is not harmful to the compound or the support, and under impregnation conditions that provide improved imbibing of the compound solution or dispersion into the support. This results in a thin, even coating of the compound on the support. The support with the solution/dispersion is dried with or without heat to form the membrane. If desired, thin films of the solid electrolytes can be laminated to one or both sides of impregnated porous support to prevent bulk flow through the membrane that can occur if large pores remain in the membrane after impregnation. It is preferred for the compound to be present as a continuous phase within the membrane.

In a fourth method the solid electrolyte may be imbibed in-situ into inorganic materials such as glass paper. The glass or other porous membranes first absorb aqueous $ZrOCl_2$ solution, and may then be immersed in a solution of $(HO)_2OPZ_q\text{-}Y_nX$ to form a supporting membrane containing the electrolyte.

Fuel Cell:

As shown in FIG. 1, the fuel cell comprises a catalyst coated membrane (CCM) (10) in combination with at least one gas diffusion backing (GDB) (13) to form an unconsolidated membrane electrode assembly (MEA). The catalyst coated membrane (10) comprises an ion exchange polymer membrane (11) discussed above and catalyst layers or electrodes (12) formed from a electrocatalyst coating composition. The fuel cell is further provided with an inlet (14) for fuel, such as liquid or gaseous alcohols, e.g. methanol and ethanol, or hydrogen; an anode outlet (15); a cathode gas inlet (16); a cathode gas outlet (17); aluminum end blocks (18) tied together with tie rods (not shown); a gasket for sealing (19); an electrically insulating layer (20); graphite current collector blocks with flow fields for gas distribution (21); and gold plated current collectors (22).

The fuel cell utilizes a fuel source that may be in the liquid or gaseous phase, and may comprise hydrogen, or an alcohol. Typically a methanol/water solution is supplied to the anode compartment and air or oxygen supplied to the cathode compartment.

Catalyst Coated Membrane (CCM):

A variety of techniques are known for CCM manufacture which apply an electrocatalyst coating composition similar to that described above onto the solid fluorinated polymer electrolyte membrane. Some known methods include spraying, painting, patch coating and screen, decal, pad or flexographic printing.

In one embodiment of the invention, the MEA (30), shown in FIG. 1, may be prepared by thermally consolidating the gas diffusion backing (GDB) with a CCM at a temperature of under 200° C., preferably 140-160° C. The CCM may be made of any type known in the art. In this embodiment, an MEA comprises a solid electrolyte (SPE) membrane with a thin catalyst-binder layer disposed thereon. The catalyst may be supported (typically on carbon) or unsupported. In one method of preparation, a catalyst film is prepared as a decal by spreading the catalyst ink on a flat release substrate such as Kapton® polyimide film (available from the DuPont Company). After the ink dries, the decal is transferred to the surface of the SPE membrane by the application of pressure and heat, followed by removal of the release substrate to form a catalyst coated membrane (CCM) with a catalyst layer having a controlled thickness and catalyst distribution. Alternatively, the catalyst layer is applied directly to the membrane, such as by printing, and then the catalyst film is dried at a temperature not greater than 200° C.

The CCM, thus formed, is then combined with a GDB to form the MEA (30). The MEA is formed, by layering the CCM and the GDB, followed by consolidating the entire structure in a single step by heating to a temperature no greater than 200° C., preferably in the range of 140-160° C., and applying pressure. Both sides of the MEA can be formed in the same manner and simultaneously. Also, the composition of the catalyst layer and GDB could be different on opposite sides of the membrane.

The invention is further illustrated by the following examples.

EXAMPLES

Method of Measuring Through-Plane, High-temperature, No-water-added Membrane Conductivity:

The conductivity of the pellets or films was measured by a technique in which the current flows through (perpendicular to) the plane of the pellet or films. A lower electrode was formed from a 12.7 mm diameter stainless steel rod and an upper electrode was formed from a 6.35 mm diameter stainless steel rod. The rods were cut to length, their ends polished, and then they were gold plated. A stack was formed consisting of lower electrode/GDE/film/GDE/upper electrode. The GDE (gas diffusion electrode) was obtained from DeNora E-TEK, Somerset, N.J., and was a catalyzed ELAT® comprising carbon cloth, a microporous layer, Pt catalyst, and a 0.6-0.8 $mg/cm^2$ Nafion® application over the catalyst layer. The lower GDE was punched out as a 9.5 mm diameter disk, while the film and the upper GDE were punched out as 6.35 mm diameter disks to match the upper electrode. The stack was assembled and held in place in a block of machinable glass ceramic (Corning MACOR®) that had a 12.7 mm diameter hole drilled into the bottom of the block, that accepted the lower electrode. A concentric 6.4 mm diameter hole was drilled into the top of the block, that accepted the upper electrode. A force of 270 N was applied to the stack by means of a clamp and calibrated spring. This produced a pressure of 8.6 MPa in the active area under the upper electrode, insuring low impedance ionic contact of the GDE's to the film. The fixture was placed in an oven for measurements at temperatures of 25° C. to 180° C. The real part of the AC impedance of the fixture containing the sample film was measured at a frequency of 100 kHz ($R_s$) using a potentiostat/frequency response analyzer (PC4/750™ potentiostat with EIS software), (Gamry Instruments, Warminster, Pa.). The fixture short ($R_f$) was also determined by measuring the real part of the 100 kHz AC impedance of the fixture assembled with the stack and both GDE's, but without the film. The conductivity was calculated as $$\kappa = t/((R_s - R_f) \times 0.317\ cm^2),$$

where t was the thickness of the pellets or films in cm.

Method of Measuring In-plane Membrane Conductivity:

The membrane sample was loaded on a four point conductivity probe. The probe has a base plate that measures 1.9"×1.5"×0.385" and a cover plate 1.9"×1.23"×0.25". Four 0.5" long platinum wires (30 GA, Hauser and Miller Precious Metals) were fixed on top of four 0.05" wide ridges along the width direction of the base plate. The outer two probes has a spacing of 1" and the inner two probes has a spacing of 0.4". In between the ridges, the space was open so that the membrane was exposed to the environment. The membrane sample, typically 1 cm wide and 3.25 cm long was pressed against the four platinum probes with the cover plate by a clamp. The membrane was also exposed to the environment on the cover plate side, which also had the openings. The four platinum wires were connected electrically to a Solatron® impedance measurement system consisting of a SI1287 electrochemical interface and a 1255B frequency response analyzer. To measure the membrane conductivity, the probe was dipped into a 500 mL glass beaker filled with the desired solution so that the membrane was fully exposed to the solution. The glass beaker was wrapped with heating tape, which was connected to a digital thermal controller. The thermocouple of the controller was immersed in the solution so that the solution temperature was precisely controlled.

Since the solution itself may have finite conductivity, it was important to correct for that in the measurement. This was accomplished by measuring separately the resistances of the cell when the membrane sample was loaded (R) and when a thin Teflon® film was loaded ($R_0$). The resistance (Rs) due to the sample was then calculated by the formula: $Rs=R \times R_0/(R_0-R)$. The sample membrane conductivity was then calculated by the formula: $\sigma=L/(Rs \times A)$ where $\sigma$ was conductivity (S/cm), L (cm) was the spacing between the inner two wires and A (cm$^2$) was the cross sectional area of the membrane.

Example 1

$(EtO)_2POCH_2CH_2CH_2CF_2CO_2Et$ was prepared using the following procedure:

A flask was charged with 4.0 g of $NiCl_2/6H_2O$, 13.0 g of Zn powder, 200 mL of THF and 3 mL of water. The resulting mixture was stirred at room temperature for 30 min, 35.0 g of diethyl allylphosphonate and 50.0 g of $ICF_2CO_2Et$ were added, the mixture was stirred at room temperature overnight, and then poured into aqueous $NH_4Cl$ solution. Solid was removed by filtration and the filtrate was extracted with ether (300 mL×3). The combined ether layers were washed with water, dried over $MgSO_4$. After removal of the ether, the residue was distilled to give 19.4 g of the title product, bp 113° C./5 mmHg. $^1H$ NMR: 4.25 (q, J=7 Hz, 2H), 4.01 (m, 4H), 2.10 (m, 2H), 2.75 (m, 4H), 1.30 (m, 9H). $^{19}F$ NMR: −105.6 (m). HRMS: Calcd. for $C_{11}H_{21}O_5F_2P_1$: 303.1173. Found: 303.1169.

$(EtO)_2POCH_2CH_2CH_2CF_2CO_2Et$ was used to prepare $(HO)_2POCH_2CH_2CH_2CF_2CO_2H$ using the following procedure:

A mixture of 19.0 g of $(EtO)_2POCH_2CH_2CH_2CF_2CO_2Et$ and 50 mL of conc. HCl was refluxed for 7 days. After removal of all volatiles, the residue was dried under vacuum to give 11.8 g of the title compound.

A glass tube was charged with the title compound and water in a ratio of 85 to 1 by weight. A liquid conductivity probe was inserted into the tube and the unsealed tube was mounted in a controlled-temperature oven. The AC impedance was measured at 1 kHz as the tube was twice heated to 150° C. and cooled in 25° C. steps. The following conductivities were calculated using a cell constant for the probe measured using a NIST traceable conductivity calibration standard for 0.1 siemens. The sample has conductivity of 129 mS/cm at 80° C. and 4.69 mS/cm at 120° C.

$(HO)_2POCH_2CH_2CH_2CF_2CO_2H$ was used to prepare $Zr(O_3PCH_2CH_2CH_2CF_2CO_2H)_2$ using the following procedure:

1.6 g (5 mmol) of $ZrOCl_2/8H_2O$ was dissolved in 30 mL of water and 4.5 mL of 50% HF and then poured in to a solution of 2.18 g (10 mmol) of $(HO)_2OPCH_2CH_2CH_2CF_2CO_2H$ in 20 mL of water. After being stirred at 70-80° C. for 3 days and at room temperature for 16 hrs, the resulting mixture was transferred into a glass tube and centrifuged. Solids were separated and washed with water thrice, and dried in a vacuum oven at 90° C. to give 2.3 g of $Zr(O_3PCH_2CH_2CH_2CF_2CO_2H)_2$. The pellet (0.3 cm diameter in size) was pressed at room temperature and conductivity, measured using the procedure described above, was found to be 0.01 mS/cm at 150° C.

Example 2

$(HO)_2OPCH_2CH_2CH_2CF_2PO(OH)_2$ was prepared using the following procedure:

A mixture of 28.51 g of diethyl allylphosphonate, 47.1 g of $ICF_2PO(OEt)_2$, 0.98 g of Cu powder in 120 mL of $CH_3CN$ was stirred at 80° C. for 8 hours. After removal of volatiles, the residue was diluted with ether, filtered, evaporated to give 61.0 g of $(EtO)_2OPCH_2CHICH_2CF_2PO(OEt)_2$. HRMS: calcd. for $C_{11}H_{21}O_5F_2P_1$: 303.11729. Found: 303.11686.

A flask was charged with 0.24 g of $NiCl_2/6H_2O$, 2.0 g of Zn powder, 100 mL of THF and 0.5 mL of water. The resulting mixture was stirred at room temperature for 20 min. 9.2 g of $(EtO)_2OPCH_2CHICH_2CF_2PO(OEt)_2$ were added and the mixture was stirred at room temperature overnight and then filtered. The filtrate was evaporated and the residue was diluted with ether, washed with aqueous $NH_4Cl$ solution, water and dried over $MgSO_4$. After removal, 3.95 g of the ether, $(EtO)_2OPCH_2CH_2CH_2CF_2PO(OEt)_2$, were obtained. A mixture of 3.95 g of $(EtO)_2OPCH_2CH_2CH_2CF_2PO(OEt)_2$ and 40 mL of conc. HCl was refluxed for 2 days, and then evaporated and dried to give 2.8 g of product. $^{19}F$ NMR: −112.9 (dt, J=102 Hz, J=18.8 Hz). $^1H$ NMR: 2.1 (m, 2H), 1.70 (m, 4H).

$Zr[O_3PCH_2CH_2CH_2CF_2PO(OH)_2]_2$ was prepared using the following procedure:

0.71 g (2.2 mmol) of $ZrOCl_2/6H_2O$ was dissolved in 8 mL of water and 1.0 mL of 50% HF and then poured into a solution of 1.1 g (4.3 mmol) of $(HO)_2OPCH_2CH_2CH_2CF_2PO(OH)_2$ in 17 mL of water. After being stirred at 70-80° C. f, or 20 hr, and at room temperature for 24 hr, the resulting mixture was transferred into a glass tube and centrifuged. Solids were separated and washed with water thrice, and dried in a vacuum oven at 100° C. to give 0.71 g of $Zr[O_3PCH_2CH_2CH_2CF_2PO(OH)_2]_2$.

The pellet was pressed at room temperature and conductivity (through plane) at 125° C., measured using the procedure described above, was found to be 27.98 mS/cm.

Example 3

$(EtO)_2OPCH_2CH_2CF_2CF_2OCF_2CF_2SO_2F$ was prepared using the following procedure:

A mixture of 110.6 g of diethyl allylphosphonate, 277.6 g of $ICF_2CF_2OCF_2CF_2SO_2F$ was heated to 80 to 85° C. under $N_2$. 0.5 g of benzoyl peroxide was added and the reaction mixture was stirred for 1.5 hr. Additional 0.5 g of benzoyl peroxide was added and the mixture was stirred for 2 hr and these steps were repeated four more times. GC indicated no starting materials. The mixture was evaporated to remove excess diethyl allylphosphonate. 120 mL of $Bu_3SnH$ were added and the mixture was stirred until no starting material remained. It was then diluted with ether, and treated with aqueous KF solution to remove $Bu_3SnI$, washed with water and dried over $MgSO_4$. After removal of the ether, 159.3 g of product were obtained. $^{19}F$ NMR: +44.4 (s, 1F), −83.7 (m, 2F), −88.9 (m, 2F), −113.2 (s, 2F), −118.8 (m, 2F). HRMS: Calcd for $C_{11}H_{16}O_6F_9P_1S_1$: 479.03398: Found: 479.03253.

$(HO)_2OPCH_2CH_2CH_2CF_2CF_2OCF_2CF_2SO_2F$ was prepared using the following procedure:

A mixture of 46.9 g of $(EtO)_2OPCH_2CH_2CH_2CF_2CF_2OCF_2CF_2SO_2F$ and conc. 200 mL of concentrated HCl was heated at 110° C. for 4 days and evaporated to remove volatile to give product. $^{19}$F NMR: +44.7 (s, 1F), −83.3 (m, 2F), −87.7 (m, 2F), −112.9 (s, 2F), −118.3 (m, 2F).

(HO)$_2$OPCH$_2$CH$_2$CH$_2$CF$_2$CF$_2$OCF$_2$CF$_2$SO$_3$H was prepared using the following procedure:

A mixture of 10.0 g of (EtO)$_2$OPCH$_2$CH$_2$CH$_2$CF$_2$CF$_2$OCF$_2$CF$_2$SO$_2$F and 2.5 g of LiOH in 60 mL of MeOH was stirred overnight and then filtered and evaporated to give solids, which were boiled with dry CH$_3$CN (3×60 mL), filtered and the filtrates were evaporated to give 10.1 g of product. $^{19}$F NMR indicated no sulfonyl fluoride peak. The solids were refluxed with 80 mL of conc. HCl for 2 days. After removal of volatiles, 8.2 grams of residue were obtained. $^{19}$F NMR: −82.9 (m, 2F), −88.5 (s, 2F), −118.0 (m, 2F), −118.5 (s, 2F). 7.2 g of solids were dissolved in water and run through an ion exchange column at two drops per minute and then evaporated and dried at 100° C. in full vacuum to give 6.65 g of wax solids.

Zr[O$_3$PCH$_2$CH$_2$CH$_2$CF$_2$CF$_2$OCF$_2$CF$_2$SO$_3$H]$_2$ was prepared using the following procedure:

0.39 g (1.2 mmol) of ZrOCl$_2$/8H$_2$O was dissolved in 5 mL of water and then poured in to a solution of 1.0 g (2.38 mmol) of (HO)$_2$OPCH$_2$CH$_2$CH$_2$CF$_2$CF$_2$OCF$_2$CF$_2$SO$_3$H in 5 mL of water. After being stirred at 70-80° C. for 20 hours, the mixture was then heated in a vacuum oven at 85° C. for 54 hrs and at 110° C. for 6 hrs. 1.03 g of brown solid were obtained, that were ground into a fine powder, and pressed into pellets. Conductivity, measured using the procedure described above, was found to be 15.10 mS/cm at 150° C.

Example 4

Benzimidazolyl-2-ethylenephosphonic acid was prepared using the following procedure:

A mixture of 10.8 g (0.1 mol) of 20.6 mL (0.093 mol), 41.7 g of concentration HCl and 41.7 g of water was refluxed 15 hr and then neutralized with 50% NaOH to pH=14. The reaction mixture was extracted with CH$_2$Cl$_2$ (3×100 mL) and aqueous layer comprised of (sodium benzimidazolyl-2-ethylenephosphonate) was treated with concentrated HCl to pH=5. Solids were filtered, washed with water for five times, dried in air and then in a vacuum oven at 60° C. for 24 hr to give 15.6 g of product.

Zr(benzimidazolyl-2-ethylenephosphonate) was prepared using the following procedure:

A solution of 1.5 g of benzimidazolyl-2-ethylenephosphonic acid in 35 mL of water and 7 mL of con. HCl was poured into a solution of 0.806 g (2.5 mmol) of ZrOCl26H2O. The resulting mixture was stirred at 80° C. for 16 hrs and at room temperature for 48 hrs. After removal of the liquid, the solid was washed with aqueous NaOH to a pH=8, and then washed with water and dried in a vacuum oven to give 1.5 g of powder. This was pressed to a pellet with thickness of 0.885 mm. Conductivity, measured using a through-plane high temperature conductivity measurement technique described above, was 1.45 mS/cm at 100° C. and 2.30 mS/cm at 125° C.

Zr(benzimidazolyl-2-ethylenephosphonate) in the presence of HF was prepared using the following procedure:

A solution of 4.5 g of benzimidazolyl-2-ethylenephosphonic acid in 50 mL of water and 12 mL of conc. HCl was poured into a solution of 3.22 g (10.0 mmol) of ZrOCl$_2$/6H$_2$O, 5.1 mL of 51% HF and 20 mL of water. The resulting mixture was stirred at 80° C. for 18 hrs and at room temperature for 24 hr, and then transferred into a glass tube and centrifuged. After removal of the top layer, the white solid was dried in a vacuum oven at 90° C. for 24 hr and suspended in EtOH. The suspension was neutralized with 10% KOH solution to pH=8.5. The solid was collected after centrifugation, washed with water and dried in the vacuum oven at 90° C. to give 1.93 g of white solid, that was pressed into a pellet with a thickness of 0.887 mm. Conductivity, measured using the procedure described above, was found to be 1.80 mS/cm at 100° C.

Example 5

This example used a modified ceramic fiber sheet, product # ASPA-1, from ZIRCAR ceramics, Inc., Florida, N.Y. The sheet nominally contained 51 wt % silica, 45 wt % alumina, and 4% hydrocarbon binder. The original binder was burned off in an 800° C. furnace for 4 hours. The sheet was then saturated with a 2% solution of Kynar® 741 PVDF resin (Atofina Chemicals, Inc., Philadephia, Pa.) in dimethylacetamide, allowed to sit for 5 minutes, and dried in a vacuum oven at 110° C. for 1 hour. The sheet was immersed in a solution of 2.6 g of ZrOCl$_2$ and 25 mL of water at room temperature overnight. The film was transferred into a solution of 1.5 g of (HO)$_2$POCH$_2$CH$_2$CH$_2$CF$_2$CO$_2$H in 20 mL of water at 85° C. for 8 hr and at held at room temperature for 2 days. The film was removed and washed with de-ionized water 5 times and dried in a vacuum oven at 100° C. overnight to give a membrane weighing 0.760 g (137% weight increase).

The membrane was loaded in an in-plane conductivity test cell containing a four-point probe as described above. The probe fixture placed four parallel platinum wires in contact with the sample. Current was measured though the outer wires while the voltage response was measured across a 1 cm gap between the inner wires. The AC impedance was measured at 1 kHz, where the impedance is dominated ionic conductance. The film had conductivity 30 mS/cm at 80° C.

What is claimed is:

1. A compound having the following structure:

wherein
X=a functional group selected from the group consisting of CO$_2$H, PO(OH)$_2$, SO$_3$H, and SO$_2$NHSO$_2$W, wherein W=aryl of 6 to 10 carbon atoms or Y;
Y=perfluoro-linear, branched or cyclic alkylene group, wherein the alkylene is 1-20 carbon atoms, or a fluorinated group containing at least one substituent selected from the group consisting of oxygen, chlorine and bromine;
Z=alkylene of 1-12 carbon atoms, aryl of 6-10 carbon atoms, or a heterocyclic aryl group of 3-10 carbons atoms;
R=alkyl of 1-12 carbon atoms, aryl of 6-10 carbon atoms, substituted alkyl, or substituted aryl, wherein the substituent is selected from the group consisting of F, Cl, perfluoroalkyl, alkyl of 1-12 carbon atoms and aryl of 6-10 carbon atoms;
n=0 or 1;
q=0 or 1; and
m=0 to 1.5; with the proviso that when n=0, and q=1, Z=at least one heterocyclic group having 3 to 10 carbon atoms, 1 to 5 nitrogen atoms and 0 to 4 oxygen atoms.

2. The compound of claim 1 wherein Y=perfluoro-linear, branched or cyclic alkylene group, wherein the alkylene is selected from the group consisting of perfluoromethylene, perfluoroethylene and perfluoropropylene.

3. The compound of claim 1 wherein Y is CF$_2$CF$_2$OCF$_2$CF$_2$ or CF$_2$CFCF$_3$OCF$_2$CF$_2$.

4. The compound of claim 1 wherein Z=a heterocyclic aryl group comprising 3 to 8 carbon atoms, 1 to 5 nitrogen atoms, and 0 to 4 oxygen atoms.

5. The compound of claim 4 wherein the heterocyclic aryl group comprises 3 to 8 carbon atoms, 2 to 3 nitrogen atoms, and 0 to 2 oxygen atoms.

6. The compound of claim 4 wherein Z is selected from the group consisting of benzimidazole, imidazole, pyrazole, triazole, thiazole, and oxadiazole.

7. The compound of claim 1 wherein R is selected from the group consisting of methyl, ethyl, propyl, butyl and phenyl.

8. The compound of claim 1 selected from the group consisting of $Zr(HO_2CCF_2CH_2CH_2CH_2PO_3)_2$, $Zr(H_2O_3PCF_2CH_2CH_2CH_2PO_3)_2$, $Zr(HO_3SCF_2CF_2OCF_2CF_2CH_2CH_2CH_2PO_3)_2$, Zirconium(2-benzimidazolyl-2-ethylphosphonate), Zirconium(2-imidazolyl-2-ethylphosphonate), Zirconium(2-pyrazolyl-2-ethylphosphonate), and Zirconium(2-oxadiazolyl-2-ethylphosphonate).

9. A solid electrolyte membrane comprising a compound having the following structure:

$$Zr(O_3PZ_qY_nX)_{2-m}(O_3PR)_m$$

wherein
X=a functional group selected from the group consisting of $CO_2H$, $PO(OH)_2$, $SO_3H$, and $SO_2NHSO_2W$, wherein W=aryl of 6 to 10 carbon atoms or Y;
Y=perfluoro-linear, branched or cyclic alkylene group, wherein the alkylene is 1-20 carbon atoms, or a fluorinated group containing at least one substituent selected from the group consisting of oxygen, chlorine and bromine;
Z=alkylene of 1-12 carbon atoms, aryl of 6-10 carbon atoms, or a heterocyclic aryl group of 3-10 carbons atoms;
R=alkyl of 1-12 carbon atoms, aryl of 6-10 carbon atoms, substituted alkyl, or substituted aryl, wherein the substituent is selected from the group consisting of F, Cl, perfluoroalkyl, alkyl of 1-12 carbon atoms and aryl of 6-10 carbon atoms;
n=0 or 1;
q=0 or 1; and
m=0 to 1.5; with the proviso that when n=0, and q=1, Z=at least one heterocyclic group having 3 to 10 carbon atoms, 1 to 5 nitrogen atoms and 0 to 4 oxygen atoms.

10. The solid electrolyte membrane of claim 9 further comprising a porous support.

11. The solid electrolyte membrane of claim 9 wherein Y=perfluoro-linear, branched or cyclic alkylene group, wherein the alkylene is selected from the group consisting of perfluoromethylene, perfluoroethylene and perfluoropropylene.

12. The solid electrolyte membrane of claim 9 wherein Y is $CF_2CF_2OCF_2CF_2$ or $CF_2CFCF_3OCF_2CF_2$.

13. The solid electrolyte membrane of claim 9 wherein Z=a heterocyclic aryl group comprising 3 to 8 carbon atoms, 1 to 5 nitrogen atoms, and 0 to 4 oxygen atoms.

14. The solid electrolyte membrane of claim 13 wherein the heterocyclic aryl group comprises 3 to 8 carbon atoms, 2 to 3 nitrogen atoms, and 0 to 2 oxygen atoms.

15. The solid electrolyte membrane of claim 13 wherein Z is selected from the group consisting of benzimidazole, imidazole, pyrazole, triazole, thiazole, and oxadiazole.

16. The solid electrolyte membrane of claim 9 wherein R is selected from the group consisting of methyl, ethyl, propyl, butyl and phenyl.

17. The solid electrolyte membrane of claim 9 wherein the compound is selected from the group consisting of $Zr(HO_2CCF_2CH_2CH_2CH_2PO_3)_2$, $Zr(H_2O_3PCF_2CH_2CH_2CH_2PO_3)_2$, $Zr(HO_3SCF_2CF_2OCF_2CF_2CH_2CH_2CH_2PO_3)_2$, Zirconium(2-benzimidazolyl-2-ethylphosphonate), Zirconium(2-imidazolyl-2-ethylphosphonate), Zirconium(2-pyrazolyl-2-ethylphosphonate), and Zirconium(2-oxadiazolyl-2-ethylphosphonate).

18. A catalyst coated membrane comprising a solid electrolyte membrane having a first surface and a second surface, an anode present on the first surface of the solid electrolyte membrane, and a cathode present on the second surface of the solid electrolyte membrane, wherein the solid electrolyte membrane comprises a compound having the following structure:

$$Zr(O_3PZ_qY_nX)_{2-m}(O_3PR)_m$$

wherein
X=a functional group selected from the group consisting of $CO_2H$, $PO(OH)_2$, $SO_3H$, and $SO_2NHSO_2W$, wherein W=aryl of 6 to 10 carbon atoms or Y;
Y=perfluoro-linear, branched or cyclic alkylene group, wherein the alkylene is 1-20 carbon atoms, or a fluorinated group containing at least one substituent selected from the group consisting of oxygen, chlorine and bromine;
Z=alkylene of 1-12 carbon atoms, aryl of 6-10 carbon atoms, or a heterocyclic aryl group of 3-10 carbons atoms;
R=alkyl of 1-12 carbon atoms, aryl of 6-10 carbon atoms, substituted alkyl, or substituted aryl, wherein the substituent is selected from the group consisting of F, Cl, perfluoroalkyl, alkyl of 1-12 carbon atoms and aryl of 6-10 carbon atoms;
n=0 or 1;
q=0 or 1; and
m=0 to 1.5; with the proviso that when n=0, and q=1, Z=at least one heterocyclic group having 3 to 10 carbon atoms, 1 to 5 nitrogen atoms and 0 to 4 oxygen atoms.

19. The catalyst coated membrane of claim 18 wherein the solid electrolyte membrane further comprising a porous support.

20. The catalyst coated membrane of claim 18 wherein Y=perfluoro-linear, branched or cyclic alkylene group, wherein the alkylene is selected from the group consisting of perfluoromethylene, perfluoroethylene and perfluoropropylene.

21. The catalyst coated membrane of claim 18 wherein Y is $CF_2CF_2OCF_2CF_2$ or $CF_2CFCF_3OCF_2CF_2$.

22. The catalyst coated membrane of claim 18 wherein Z=a heterocyclic aryl group comprising 3 to 8 carbon atoms, 1 to 5 nitrogen atoms, and 0 to 4 oxygen atoms.

23. The catalyst coated membrane of claim 22 wherein the heterocyclic aryl group comprises 3 to 8 carbon atoms, 2 to 3 nitrogen atoms, and 0 to 2 oxygen atoms.

24. The catalyst coated membrane of claim 22 wherein Z is selected from the group consisting of benzimidazole, imidazole, pyrazole, triazole, thiazole, and oxadiazole.

25. The catalyst coated membrane of claim 18 wherein R is selected from the group consisting of methyl, ethyl, propyl, butyl and phenyl.

26. The catalyst coated membrane of claim 18 wherein the compound is selected from the group consisting of $Zr(HO_2CCF_2CH_2CH_2CH_2PO_3)_2$, $Zr(H_2O_3PCF_2CH_2CH_2CH_2PO_3)_2$, $Zr(HO_3SCF_2CF_2OCF_2CF_2CH_2CH_2CH_2PO_3)_2$, Zirconium(2-benzimidazolyl-2-ethylphosphonate), Zirconium(2-imidazolyl-2-ethylphosphonate), Zirconium(2-pyrazolyl-2-ethylphosphonate), and Zirconium(2-oxadiazolyl-2-ethylphosphonate).

27. A fuel cell comprising a solid electrolyte membrane having a first surface and a second surface, wherein the solid electrolyte membrane comprises a compound having the following structure:

$$Zr(O_3PZ_qY_nX)_{2-m}(O_3PR)_m$$

wherein
- X=a functional group selected from the group consisting of $CO_2H$, $PO(OH)_2$, $SO_3H$, and $SO_2NHSO_2W$, wherein W=aryl of 6 to 10 carbon atoms or Y;
- Y=perfluoro-linear, branched or cyclic alkylene group, wherein the alkylene is 1-20 carbon atoms, or a fluorinated group containing at least one substituent selected from the group consisting of oxygen, chlorine and bromine;
- Z=alkylene of 1-12 carbon atoms, aryl of 6-10 carbon atoms, or a heterocyclic aryl group of 3-10 carbons atoms;
- R=alkyl of 1-12 carbon atoms, aryl of 6-10 carbon atoms, substituted alkyl, or substituted aryl, wherein the substituent is selected from the group consisting of F, Cl, perfluoroalkyl, alkyl of 1-12 carbon atoms and aryl of 6-10 carbon atoms;
- n=0 or 1;
- q=0 or 1; and
- m=0 to 1.5; with the proviso that when n=0, and q=1, Z=at least one heterocyclic group having 3 to 10 carbon atoms, 1 to 5 nitrogen atoms and 0 to 4 oxygen atoms.

28. The fuel cell of claim 27 further comprising an anode and a cathode present on the first and second surfaces of the solid electrolyte membrane.

29. The fuel cell of claim 28 further comprising gas diffusion backings adjacent the anode and cathode.

30. The fuel cell of claim 27 further comprising gas diffusion electrodes comprising a gas diffusion backing and an electrode present on the first and second surfaces of the solid polymer electrolyte membrane, wherein the electrode is adjacent the solid polymer electrolyte membrane.

31. The fuel cell of claim 28 further comprising a means for delivering fuel to the anode, a means for delivering oxygen to the cathode, a means for connecting the anode and cathode to an external electrical load, methanol in the liquid or gaseous state in contact with the anode, and oxygen in contact with the cathode.

32. The fuel cell of claim 27 wherein the fuel is hydrogen.

33. The fuel cell of claim 27 wherein the fuel is an alcohol.

34. The fuel cell of claim 33 wherein the fuel is methanol.

* * * * *